United States Patent [19]

Horn et al.

[11] 3,970,648

[45] July 20, 1976

[54] 2-[2-(5-NITRO-2-FURYL)VINYL]-4-(ANILINO)QUINAZOLINES

[75] Inventors: Herman Horn, Staten Island, N.Y.; Sheldon B. Greenbaum, Livingston; Charles M. Ely, Berkeley Heights, both of N.J.; Walter Hacke, New York, N.Y.; David A. Olle, North Arlington, N.J.

[73] Assignee: Diamond Shamrock Corporation, Cleveland, Ohio

[22] Filed: Sept. 6, 1974

[21] Appl. No.: 503,854

[52] U.S. Cl. .................... 260/240 A; 260/251 Q
[51] Int. Cl.² ........................... C07D 405/06
[58] Field of Search ...... 260/240 A, 251 Q, 251 QA

[56] References Cited

UNITED STATES PATENTS

| | | | |
|---|---|---|---|
| 3,359,262 | 12/1967 | Takamatsu et al. | 260/240 A |
| 3,542,784 | 11/1970 | Burch | 260/251 Q X |
| 3,632,584 | 1/1972 | Gutsche et al. | 260/240 A |
| 3,814,758 | 6/1974 | Albrecht et al. | 260/240 A |

FOREIGN PATENTS OR APPLICATIONS

| | | | |
|---|---|---|---|
| 28,337 | 12/1964 | Japan | 260/240 A |
| 4,356 | 2/1968 | Japan | 260/240 A |
| 26,408 | 11/1964 | Japan | 260/240 A |

OTHER PUBLICATIONS

Muira – The Nitro Furans in Progress in Medical Chem. vol. 5, 1967 pp. 320–335.

*Primary Examiner*—Allen B. Curtis
*Attorney, Agent, or Firm*—Leslie G. Nunn; Neal T. Levin

[57] ABSTRACT

2-[2-(5-Nitro-2-furyl)vinyl]-4-(anilino)quinazolines and 2-[2-(5-nitro-2-furyl)vinyl]-4-(hydroxyanilino)-quinazolines are prepared and used as pesticides and animal growth promotants. These quinazolines also improve the feed efficiency of animals.

2 Claims, No Drawings

2-[2-(5-NITRO-2-FURYL)VINYL]-4-(ANILINO)-QUINAZOLINES

BACKGROUND OF THE INVENTION

1. Field of the Invention

This invention relates to new quinazolines, their preparation and use as bactericides and animal growth promotants as well as additives to improve feed efficiencies in animals.

2. Description of the Prior Art

Aside from the well known ability of certain antibiotics to increase growth and to improve the feed efficiency when used in the rearing of economic animals such as chickens and hogs, various patents and publications claim similar properties for other types of organic compounds. Often, when the latter are employed in tests where the animals are maintained at a high nutritional level under optimum conditions such as actually practiced in animal husbandry in the United States, they fail to continue to show any substantial growth promotion activity or improvement in feed efficiency.

Nitrofuran quinazolines bearing a substituted phenyl group in the 4-position of the quinazoline such as found in the prior art had the nitrofuran group directly attached to the quinazoline. These compounds showed some activity against Streptococcus faecalis, but gave only little growth promotion in some experiments and none in others. These compounds did not demonstrate any improvement in feed efficiency. One of these compounds was the product of Example III in U.S. Pat. No. 3,542,784 — Burch, 2-(5-nitro-2-furyl)-4-(p-hydroxyanilino)quinazoline. Further, it was observed that another compound of the prior art, quinazoline 1,4-dioxide showed little growth promotion and improvement of the feed efficiency in tests with animals reared under optimum conditions.

There is a definite need for organic compounds which will provide increased growth and improved feed efficiency when used in the rearing of economic animals.

SUMMARY OF THE INVENTION

It has been found that insertion of a vinyl group between the nitrofuran and quinazoline rings not only gives a marked increase in the activity against Streptococcus faecalis but also gives compounds with useful growth promoting properties and a marked improvement in feed efficiency when incorporated in animal feeds in experiments with animals in a highly adequate nutritional state. These compounds, the 2-[2-(5-nitro-2-furyl)vinyl]-4-(anilino)quinazolines are prepared by reaction of 2-[2-(5-nitro-2-furyl)vinyl]-4-chloroquinazoline with aniline or an aminophenol. These quinazolines have the following formula:

wherein X is a hydrogen, o-hydroxy, m-hydroxy and p-hydroxy radical.

These compounds are effective as bactericides against bacteria such as S. faecalis and are also useful in eliciting improved growth and feed efficiency when added to animal feeds.

DESCRIPTION OF THE PREFERRED EMBODIMENTS

Useful 2-[2-(5-nitro-2-furyl)vinyl]-4-(anilino)-quinazolines include

2-[2-(5-nitro-2-furyl)vinyl]-4-(anilino)quinazoline
2-[2-(5-nitro-2-furyl)vinyl]-4-(p-hydroxyanilino)-quinazoline
2-[2-(5-nitro-2-furyl)vinyl]-4-(o-hydroxyanilino)-quinazoline
2-[2-(5-nitro-2-furyl)vinyl]-4-(m-hydroxyanilino)-quinazoline These quinazolines enhance the performance of animals such as poultry, swine and cattle. They increase growth rate, improve feed efficiency and reduce losses which occur in animals during periods of stress such as weaning, high environmental temperature and moving.

Addition of these quinzolines to typical animal feed formulas yield animal feeds which produce the desirable results of growth promotion, feed efficiency improvement and stress alleviation in animals. If desired, a premix may be prepared by mixing the quinazoline with a suitable carrier or an aliquot of animal feed. The premix may be prepared using carriers such as soybean meal, alfalfa meal, cotton seed oil meal, linseed oil meal, cornmeal, cane molasses, urea, bone meal and corncob meal as well as any other suitable ingredient used in formulation of the feed. When a premix is used, it is much easier to obtain uniform distribution of the quinazoline in the feed.

The proportion of quinazoline used in the premix may be varied over fairly wide limits, because the amount in the finished feed can be adjusted by blending an appropriate amount of the premix to obtain the desired dosage. The advantage of the premix is that the feed manufacturer may blend the premix with other ingredients as carriers to produce feed supplements or concentrated feeds having the desired quinazoline level. The premix may then be added directly to the basal ration which contains sufficient protein, fat, fiber, carbohydrates, vitamins and minerals to meet the nutritional requirements of the animal for which the feed is intended. Most of these substances are present in naturally occurring feed materials such as alfalfa meal, corn meal, soybean meal, oats, wheat and wheat by-pro-

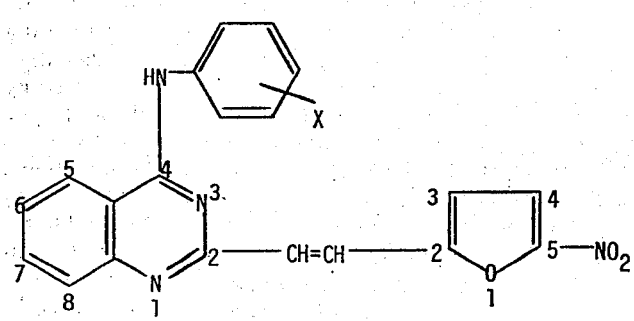

ducts, cane molasses and the like. Frequently, iodized salt, bone meal, trace minerals and urea in cattle feeds may be added to furnish needed minerals and additional nitrogen. The premix may be also used as a top dressing to feed or any roughage such as hay, silage, ground corncobs which are fed to the animals. If desired, the quinazoline may be formulated in liquid form so it can be administered to the animal in the form of drink or liquid food. The quantity of quinazoline in the finished feed may vary from about 10 g to about 200 g per ton of feed, with a preferred level of about 10 g to 50 g per ton of feed. If desired, other dietary supplements such as antibiotics, sulfa drugs, vitamins, minerals and medicaments may be used in conjunction with the quinazoline in animal feeds.

The preferred amount of quinazoline which is present in the daily ration for poultry species (chickens, turkeys, etc.) and swine may vary from about 10 g to about 50 g per ton and for cattle, sheep and horses from about 25 mg to about 70 mg per head per day.

For a fuller understanding of the nature and objects of this invention, reference may be made to the following examples. These examples are given merely to illustrate the invention and are not to be construed in a limiting sense. All parts, proportions and quantities are by weight unless otherwise indicated. The terms g, l, °C, °F, lb, T are used to indicate grams, liters, degrees Centigrade, degrees Fahrenheit, pounds and tons respectively, in these examples. Feed efficiency, as used herein, refers to the pounds of feed required to produce a pound of body weight gain. Feed efficiency improvement, therefore, implies that less feed is required to produce a given amount of body weight gain.

EXAMPLE I

This example shows preparation of 2-[2-(5-nitro-2-furyl)vinyl]-4-(p-hydroxyanilino)quinazoline, (V). In this preparation, anthranilamide hydrochloride was converted to 2-methyl-4-(3H)quinazoline (I) and 5-nitrofurfurylidene diacetate to 5-nitro-2-furancarboxaldehyde (II); (I) and (II) were then reacted to obtain 2-[2-(5-nitro-2-furyl)vinyl]-4-(3H) quinazolinone(III); (III) was then chlorinated to obtain 2-[2-(5-nitro-2-furyl)vinyl]-4-chloroquinazoline (IV) which was reacted with p-aminophenol to obtain the desired product, 2-[2-(5-nitro-2-furyl)vinyl]-4-(p-hydroxyanilino)-quinazoline (V) and referred to in subsequent examples as the product of Example I. The procedure in this preparation is as follows:

2-Methyl-4-(3H)quinazolinone (I)

Anthranilamide hydrochloride was prepared by adding 20 ml of concentrated hydrochloric acid (37% by weight) to a solution of 27.3 g of anthranilamide in 200 ml of methanol. This mixture was cooled in an ice bath to precipitate the hydrochloride which was then collected and dried to obtain a product melting at 234°C with decomposition. A 17.4 g (0.1 mole) portion of the hydrochloride obtained above was refluxed for 3 hours with 100 ml acetic anhydride and allowed to stand overnight. The mixture was then cooled in an ice bath and the solids collected by filtration on a Buchner funnel. The filter cake was slurried in 100 ml of water, and warmed to aid solution and then 28% aqueous ammonia was added until the mixture was alkaline. After cooling the 2-methyl-4-(3H)quinazolinone precipitated as a solid, was then collected, washed with a small amount of cold water and dried at 70°C to obtain 6.72 g of the desired product. The 2-methyl-4-(3 H)quinazolinone melted at 236°–8°C and was obtained in a 42% yield.

5-nitro-2-furancarboxaldehyde (II)

A total of 86.5 g of 5-nitrofurfurylidine diacetate was added in small portions to 90 ml of sulfuric acid (73% by weight) over a period of 10 to 15 min. The mixture was stirred for 30 min at ambient temperature, 10 min at 50°C, cooled to 30°C, and then poured onto 150 g of crushed ice. The mixture was filtered, sucked as dry as possible on a Buchner funnel with the aid of a rubber dental dam and this afforded 51.5 g of 5-nitro-2-furancarboxaldehyde which melted at 32°–34°C.

2-[2-(5-nitro-2-furyl)vinyl]-4-(3H)quinazolinone (III)

To 16 g (0.1 mole) 2-methyl-4-(3H)quinazolinone were added 100 ml acetic anhydride, 0.5 ml 96% sulfuric acid and 20 g (0.14 mole) 5-nitro-2-furancarboxaldehyde and the mixture was stirred 2 hours at 50°–60°C. The reaction mixture was poured into water and boiled 10 min. After it stood overnight, the product was collected by filtration, washed with water, then methanol. A yellow solid weighing 12.50 g (44% yield) was obtained, m.p. 327°C. This solid 2-[2-(5-nitro-2-furyl)vinyl]-4-(3H)quinazolinone was used to prepare the chloro- (IV) and anilino (V) derivatives described below.

2-[2-(5-nitro-2-furyl)vinyl]-4-chloroquinazoline (IV)

A 500 ml 3 necked flask fitted with a stirrer, reflux condenser and protected by a calcium chloride trap was charged with 9.0 g of phosphorus pentachloride (0.043 mole) and 70 ml of phosphorus oxychloride and the mixture stirred. To this 11.3 g (0.04 mole) of 2-[2-(5-nitro-2-furyl)vinyl]-4-(3H)quinazolinone was added and rinsed into the flask with 15 ml of phosphorus oxychloride. The mixture was heated under reflux for 4 hours, cooled in an ice bath and diluted with 150 ml of diethyl ether. The 2-[2-(5-nitro-2-furyl)vinyl]-4-chloroquinazoline which precipitated was collected by filtration, washed with 100–150 ml of diethyl ether, slurried in 100 ml of diethyl ether and then refiltered to obtain 8.09 g of the desired product melting at 252°–4°C with decomposition. The product was recrystallized from toluene (large volumes are required) or was extracted in a Soxhlet extractor with toluene to obtain yellow crystals of 2-[2-(5-nitro-2-furyl)vinyl]-4-chloroquinazoline melting at 264°–5°C with decomposition.

Analysis. Calcd. for $C_{14}H_8ClN_3O_3$ (percent): C, 55.74; H, 2.67; N, 13.93; Cl, 11.75. Found (percent) C, 56.00; H, 3.19; N, 13.61; Cl, 11.43.

2-[2-(5-nitro-2-furyl)vinyl]-4-(p-hydroxyanilino)-quinazoline (V)

A 250 ml Erlenmeyer flask equipped with a magnetic stirrer and oil bath for heating was charged with 8.0 g (0.07 mole) of p-aminophenol and 25 ml of dimethylformamide. After the p-aminophenol was dissolved by stirring, 9.05 g (0.03 mole) of 2-[2-(5-nitro-2-furyl)-vinyl]-4-chloroquinazoline (IV) was added. The reaction mixture was then heated at 70°–90°C for 2 hours after which 60 ml of water was added and the solution after cooling was placed in a refrigerator for crystallization. After three days, the brown yellow solid was collected, washed first with water, then methanol and then dried to obtain 7.20 g of product melting at 250°–60°C with decomposition. Recrystallization from a 1:1 dimethylformamidemethanol mixture gave 6.5 g of orange crystals of the purified product which melted at 270°–2°C with decomposition.

Analysis. Calcd. for $C_{20}H_{14}N_4O_4$ (percent): C, 64.16; H, 3.76; N, 14.96. Found (percent): C, 63.77; H, 4.01; N, 14.45.

EXAMPLE II

2-[2-(5-nitro-2-furyl)vinyl]-4-(m-hydroxyanilino)-quinazoline (VI)

An Erlenmeyer flask was charged with 4.8 g (0.044 mole) of m-aminophenol and 100 ml of dimethylformamide. The charge was stirred to dissolve the m-aminophenol and 6.5 g (0.02 mole) of 2-[2-(5-nitro-2-furyl)-vinyl]-4-chloroquinazoline (IV) was added. The reaction mixture was reacted as in Example I to obtain 6.5 g of crude product, a yellow solid which melted at 241°–2°C with decomposition. A 5.5 g sample was recrystallized from 40 ml of dimethyl formamide and 74 ml of methanol was added to the warm solution which was then cooled to recrystallize. The purified product, 4.8 g of yellow needles melted at 255°–61°C with decomposition.

Analysis. Calcd. for $C_{20}H_{14}N_4O_4$ (percent): C, 64.16; H, 3.76; N, 14.96. Found (percent): C, 63.90; H, 3.83; N, 15.36.

EXAMPLE III

2-[2-(5-nitro-furyl)vinyl[-4-(o-hydroxyanilino)-quinazoline (VII)

An Erlenmeyer flask equipped with magnetic stirrer and oil bath for heating was charged with 5.0 g (0.046 mole) of o-aminophenol and 100 ml of dimethylformamide. The charge was stirred to dissolve o-aminophenol and 6.0 g (0.02 mole) of 2-[2-(5-nitro-2-furyl)-vinyl]-4-chloroquinazoline (IV) added. The reaction mixture was reacted at 80° to 90°C for 2 hours to form an orange precipitate; 100 ml of water was added to the warm mixture which was then allowed to cool and placed overnight in a refrigerator to crystallize. The solids were collected, washed with methanol and dried to obtain 7.5 g of brown-tan solid which melted 224°–6°C with decomposition. A solution of the product in 100 ml of dimethylformamide was treated with activated carbon and filtered. A first portion of 75 ml of methanol was added to the warm filtrate then an additional 25 ml portion. Cooling and scratching gave 5.5 g of orange crystals of the purified product which melted at 230°–1°C with decomposition.

Analysis. Calcd. for $C_{20}H_{14}N_4O_4$ (percent); C, 64.16; H, 3.76; N, 14.96. Found (percent); c, 63.96; H, 3.76; N, 14.97.

EXAMPLE IV

2-[2-(5-nitro-2-furyl)vinyl]-4-anilinoquinazoline (VIII)

A 250 ml flask equipped with stirrer, reflux condenser and thermometer was charged with 4.1 g (0.044 mole) aniline and 100 ml dimethyl formamide. The charge was stirred to dissolve and 6 g (0.02 mole) 2-[2-(5-nitro-2-furyl)vinyl]-4-chloroquinazoline (IV) was added. The mixture was reacted at 130°–2°C for 2 hours to form a dark red solution. A 75 ml portion of water was added to the warm solution which was allowed to stand at room temperature overnight, then cooled 1 hour in an ice bath. The crystallized solid was collected, washed with methanol and dried to yield 5.5 g of brown solid. The solid was dissolved in 50 ml warm dimethyl formamide, decolorized with activated carbon, and precipitated by adding 100 ml methanol, with cooling and scratching to induce crystallization. The precipitated solid was collected and washed with methanol to yield 3.3 g product, m.p. 183°C. This product was recrystallized from 30 ml glacial acetic acid, treated with decolorizing carbon and allowed to crystallize to yield 2.2 g of purified product, m.p. 184°–6°C.

Analysis: Calcd. for $C_{20}H_{14}N_4O_3$ (percent): C, 67.04; H, 3.94; H, 15.63. Found (percent): C, 67.93; H, 4.14; N, 15.46.

EXAMPLE V

Bactericide Test

Test formulations were examined for bactericidal and/or bacteriostatic activity against the test organisms shown in Tables A and B. These organisms were chosen as being representative of commercially important pathogens affecting animal agriculture. The antibiotic chlortetracycline was chosen as a positive control, since it has a broad spectrum of activity against a large number of organisms, and its activity can be used for comparative purposes.

Basic test formulations of the product of Examples I, II, III, and of chlortetracycline were prepared by dissolving 16 mg (0.016 g) in 2.0 ml of stock emulsifier solution (0.25% Triton X-155 in acetone by volume) and making each solution up to 50 ml with deionized water. The concentration of the test compound in the basic formulation was 320 ppm. Lower concentrations of the test compound were obtained by diluting the basic formulation with a 4% solution of the stock emulsifier in deionized water so that each dilution in the series differed only in test compound content.

Nutrient-tryptic soy agar (NTA) consisting of 2.0% Difco Bactoagar 0.8% nutrient broth (Difco), and 0.5% tryptic soy broth (Difco) was prepared and sterilized by autoclaving. A 2 ml aliquot of each test formulation was added to 8 ml of molten NTA. This mixture was then plated in a sterile polystyrene petri dish (100 × 15 mm). After the agar was set, suspensions of each of the test organisms were simultaneously streaked onto the surface of the agar. The inoculated plates were incubated for 48 hr at 28°C. The inhibition of growth of each organism was rated by visual comparison with the organism developing on non-treated agar. Growth inhibition reported as per cent control was rated in three categories as follows: 0% control, growth equivalent to that on non-treated agar; 50% control, sparse development and separated colonies; 100% control, no visible growth or development of colonies. Results of these tests are shown in Table A. These results indicate that the compounds of Examples I, II, III, and IV were considerably more effective (i.e., showed 100% inhibition and substantially lower concentrations) than chlortetracycline against *S. faecalis, E. rhusiopathiae, B. bronchiseptica, S. agalactiae, Streptococcus* group E and *Vibrio coli.*

TABLE A

BACTERICIDE TESTS
% Inhibition at Indicated Concentration (ppm)

| Product of Example | Test Organism[a] | 64 | 32 | 16 | 8 | 4 | 2 | 1 | 0.5 | 0.25 | 0.125 |
|---|---|---|---|---|---|---|---|---|---|---|---|
| I | Ec | 0 | 0 | 0 | 0 | 0 | 0 | 0 | 0 | 0 | 0 |
|  | Sa | 0 | 0 | 0 | 0 | 0 | 0 | 0 | 0 | 0 | 0 |
|  | Sf | 100 | 100 | 100 | 100 | 100 | 100 | 100 | 100 | 100 | 100 |
|  | Sc | 0 | 0 | 0 | 0 | 0 | 0 | 0 | 0 | 0 | 0 |
|  | Sg | 0 | 0 | 0 | 0 | 0 | 0 | 0 | 0 | 0 | 0 |
|  | Er | 100 | 100 | 100 | 100 | 100 | 100 | 100 | 100 | 100 | 100 |
|  | Bb | 100 | 100 | 100 | 100 | 100 | 100 | 100 | 100 | 100 | 100 |
|  | St | 0 | 0 | 0 | 0 | 0 | 0 | 0 | 0 | 0 | 0 |
|  | Sta | 100 | 100 | 100 | 100 | 100 | 100 | 100 | 100 | 100 | 100 |
|  | StE | 100 | 100 | 100 | 100 | 100 | 100 | 100 | 100 | 100 | 100 |
|  | Vc | 100 | 100 | 100 | 100 | 100 | 100 | 100 | 100 | 100 | 100 |
| II | Ec | 0 | 0 | 0 | 0 | 0 | 0 | 0 | 0 | 0 | 0 |
|  | Sa | 0 | 0 | 0 | 0 | 0 | 0 | 0 | 0 | 0 | 0 |
|  | Sf | 100 | 100 | 100 | 100 | 100 | 100 | 100 | 100 | 50 | 0 |
|  | Sc | 0 | 0 | 0 | 0 | 0 | 0 | 0 | 0 | 0 | 0 |
|  | Sg | 0 | 0 | 0 | 0 | 0 | 0 | 0 | 0 | 0 | 0 |
|  | Er | 100 | 100 | 100 | 100 | 100 | 100 | 100 | 100 | 100 | 100 |
|  | Bb | 100 | 100 | 100 | 0 | 0 | 0 | 0 | 0 | 0 | 0 |
|  | St | 0 | 0 | 0 | 0 | 0 | 0 | 0 | 0 | 0 | 0 |
|  | Sta | 100 | 100 | 100 | 100 | 100 | 100 | 100 | 100 | 100 | 100 |
|  | StE | 100 | 100 | 100 | 100 | 100 | 100 | 100 | 100 | 100 | 100 |
|  | Vc | 100 | 100 | 100 | 100 | 100 | 100 | 100 | 100 | 100 | 100 |
| III | Ec | 0 | 0 | 0 | 0 | 0 | 0 | 0 | 0 | 0 | 0 |
|  | Sa | 0 | 0 | 0 | 0 | 0 | 0 | 0 | 0 | 0 | 0 |
|  | Sf | 100 | 100 | 100 | 100 | 100 | 100 | 100 | 50 | 0 | 0 |
|  | Sc | 100 | 100 | 100 | 50 | 50 | 0 | 0 | 0 | 0 | 0 |
|  | Sg | 100 | 100 | 100 | 50 | 50 | 0 | 0 | 0 | 0 | 0 |
|  | Er | 100 | 100 | 100 | 100 | 100 | 100 | 100 | 100 | 100 | 100 |
|  | Bb | 100 | 100 | 100 | 100 | 100 | 100 | 100 | 100 | 100 | 100 |
|  | St | 0 | 0 | 0 | 0 | 0 | 0 | 0 | 0 | 0 | 0 |
|  | Sta | 100 | 100 | 100 | 100 | 100 | 100 | 100 | 100 | 100 | 100 |
|  | StE | 100 | 100 | 100 | 100 | 100 | 100 | 100 | 100 | 100 | 100 |
|  | Vc | 100 | 100 | 100 | 100 | 100 | 100 | 100 | 100 | 100 | 100 |
| CTC[b] | Ec | 100 | — | 100 | — | 0 | — | 0 | — | — | — |
|  | Sa | 100 | — | 100 | — | 0 | — | 0 | — | — | — |
|  | Sf | 100 | — | 100 | — | 100 | — | 100 | — | — | — |
|  | Sc | 100 | — | 100 | — | 0 | — | 0 | — | — | — |
|  | Sg | 100 | — | 100 | — | 0 | — | 0 | — | — | — |
|  | Er | 100 | — | 100 | — | 10 | — | 0 | — | — | — |
|  | Bb | 100 | — | 0 | — | 0 | — | 0 | — | — | — |
|  | St | 0 | — | 0 | — | 0 | — | 0 | — | — | — |
|  | Sta | 100 | — | 100 | — | 100 | — | 0 | — | — | — |
|  | StE | 100 | — | 100 | — | 0 | — | 0 | — | — | — |
|  | Vc | 100 | — | 100 | — | 100 | — | 0 | — | — | — |

[a]Code for test organisms
Ec = *Escherichia coli*
Sa = *Staphylococcus aureus*
Sf = *Streptococcus faecalis*
Sc = *Salmonella cholerasuis*
Sg = *Salmonella gallinarum*
Er = *Erysipelothrix rhusiopathiae*
Bb = *Bordetella bronchiseptica*
St = *Salmonella typhimurium*
Sta = *Streptococcus agalactiae*
StE = *Streptococcus* group E
Vc = *Vibrio coli*
[b]Chlorotetracycline

EXAMPLE VI

Bactericide Test

Test formulations of the product of Example IV were examined for bactericidal and/or bacteriostatic activity against the test organisms shown in Table B using the Bactericide Test described in Example V. The inhibition of organism growth with each diluted test formulation was rated visually by comparison with the organism developing on a non-treated control agar plate. Growth inhibition reported as per cent control was rated in three categories as follows: 0% control, growth equivalent to that on non-treated agar; 50% control is sparse development and separated colonies; and 100% control, development of individual colonies was not apparent. Results of these tests are shown in Table B.

TABLE B

Bactericide Tests with
2-[2-(5-Nitro-2-furyl)vinyl]-4-(anilino)quinazoline

| % Control In Vitro Growth at indicated ppm | Test Organism (a) | | | | |
|---|---|---|---|---|---|
|  | Ec | Sa | Sf | Sc | Sg |
| 4 | 50 | 50 | 100 | 50 | 100 |
| 2 | 50 | 50 | 100 | 50 | 100 |
| 1 | 50 | 50 | 100 | 50 | 100 |
| 0.5 | 0 | 0 | 100 | 0 | 100 |
| 0.25 | 0 | 0 | 100 | 0 | 100 |
| 0.125 | 0 | 0 | 100 | 0 | 0 |
| 0.06 | 0 | 0 | 50 | 0 | 0 |
| 0.03 | 0 | 0 | 0 | 0 | 0 |
| 0.01 | 0 | 0 | 0 | 0 | 0 |
| 0.007 | 0 | 0 | 0 | 0 | 0 |

(a) Code for test organisms
Ec = *Escherichia coli*
Sa = *Staphylococcus aureus*
Sf = *Streptococcus faecalis*
Sc = *Salmonella cholerasuis*
Sg = *Salmonella gallinarum*

EXAMPLE VII

One hundred 20 day-old broiler cross chicks were weight equalized into 15 groups of eight chicks each and placed in battery brooders. The 40 chick treatment groups (five replicates) were fed the one of the three rations described below for a 4 week period. Weekly measurements of body weights and feed consumption were made by replicate, and these measurements used to calculate weight gain and feed efficiency.

The commercial type broiler starter basal ration which was used in this study was designated as the Basal Ration, and had the following composition:

| Ingredient | Weight Percent |
| --- | --- |
| Corn meal | 55.5 |
| Soybean meal (50% protein) | 30.2 |
| Tallow | 4.75 |
| Fish meal | 3.75 |
| Meat and bone scraps | 2.5 |
| Alfalfa meal | 1.5 |
| Dicalcium phosphate | 0.75 |
| Salt | 0.3 |
| Ground limestone | 0.5 |
| Vitamin-Trace Mineral Premix | 0.25 |
| TOTAL | 100.00% |

The preceding basal ration was mixed with bacitracin at a level of 4 g/T as the only growth stimulant to simulate commercial practice. This mixture was designated as the Basal Ration + Bacitracin (4 g/T) and constituted the negative control in this study.

A second ration was prepared by fortifying the Basal Ration + bacitracin described above with the Product from Example I above at a level of 200 g/T, and was designated as Basal Ration + Bacitracin + Product of Example I (200 g/T). A third ration was prepared by fortifying the Basal Ration + bacitracin described above with chlortetracycline (CTC) at a level of 200 g/T, and was designated as Basal Ration + Bacitracin + Chlortetracycline (200 g/T). Chlortetracycline served as the positive control in this test because it had shown strong growth promotion in numerous previous tests at this therapeutic level.

A summary of the 4 week body weight gains and feed efficiencies are presented in Table I. Improvements in body weight gains and feed efficiencies were noted for the groups receiving rations fortified with the product of Example I and chlortetracycline. A statistical analysis by the standard analysis of variance method indicated that the improved weight gains (for both) was significant at the 99.5% level of probability, while the improved feed efficiencies (for both) was significant at the 99.9% level of probability. The commercial value of the product of Example I is indicated by the fact that these significant responses were obtained in addition to the growth stimulation provided by the presence of bacitracin in the ration. It is important to note that the negative controls in this example and in Examples VIII and X which follow were characterized by rapid rates of growth. This high plane of growth and feed efficiency performance on the part of the negative controls makes the responses to the test compounds all the more meaningful.

The term "growth promotion" is used herein to describe the beneficial effect of a compound in eliciting a more rapid rate of weight gain when compared to the weight gain of control animals not fed the compound. "Feed efficiency" is a term regularly used in animal husbandry and is a measure of the pounds of feed required to produce a pound of gain in the weight of the animal. A lower mathmatical value for feed efficiency reflects improved performance. To simplify comparison, the percentage improvement in feed efficiency is also calculated in the sixth (last) column in Table I by dividing the difference between the feed efficiencies of the experiment and control given in the fourth column by the feed efficiency of the control and multiplying by 100. In this case, as in the case of the weight gain (fifth column), an improved performance is indicated by a higher positive number.

TABLE I

| Group | No. Chicks | Treatment | Average 4 Week Performance | | Improved Response Over Basal Ration + Bacitracin (%) | |
| --- | --- | --- | --- | --- | --- | --- |
| | | | Gain (gms) | Feed Efficiency | Gain | Feed Efficiency |
| 1 | 40 | Basal Ration + Bacitracin (4 g/T) | 694.5 | 1.721 | — | — |
| 2 | 40 | Basal Ration + Bacitracin (4 g/T) + Product of Example I (200 g/T) | 739.8 | 1.597 | +6.5 | +7.2 |
| 3 | 40 | Basal Ration + Bacitracin (4 g/T) + Chlortetracycline (200 g/T) | 732.4 | 1.607 | +5.5 | +6.6 |

EXAMPLE VIII

This example demonstrates growth promotion activity of the Product of Example I and other growth promotants at low levels of fortification in feed. Day old broiler cross chicks were weight equalized into groups of eight chicks each and were placed in battery brooders. The 32 chick treatment groups (four replicates) were fed one of the five rations described below for a 4 week period. Weekly measurements of body weights and feed consumption were made by replicate, and these measurements used to calculate weight gain and feed efficiency.

The basal ration was the basal ration used in Example VII above. The remaining five rations were obtained by mixing the indicated quantities of bacitracin (4 g/T), chlortetracycline (10 g/T), product of Example I (10 g/T), and product of Example III of U.S. Pat. No. 3,542,784 — Burch (10 g/T) as growth promotants with the basal ration.

A summary of the 4 week body weight gains and feed efficiencies is presented in Table II. It will be noted from the results in Table II that the product of Example I showed greater growth promotion than any of the other growth promotants used in this test.

TABLE II

| Group | No. Chicks | Treatment | Average 4 Week Performance Gain (g) | Average 4 Week Performance Feed Efficiency | Improved Response Over Basal Ration (%) Gain | Improved Response Over Basal Ration (%) Feed Efficiency |
|---|---|---|---|---|---|---|
| 1 | 32 | Basal Ration | 720.4 | 1.760 | — | — |
| 2 | 32 | Basal Ration + Bacitracin (4 g/T) | 703.6 | 1.739 | −2.3 | +1.2 |
| 3 | 32 | Basal Ration + Chlorotetracycline (10 g/T) | 714.2 | 1.745 | −0.9 | +0.9 |
| 4 | 32 | Basal Ration + Product of Example I (10 g/T) | 750.7 | 1.671 | +4.2 | +5.1 |
| 5 | 32 | Basal Ration + Product of Example III of U.S. 3,542,784 — Burch (10 g/T) | 723.1 | 1.726 | +0.4 | +1.9 |

EXAMPLE IX

This example demonstrates the growth promotion activity of the product of Example I at varying concentrations (titration dosage). The concentrations used in this test were 6.25, 12.5, 25, 50, 100, 200 and 400 g of the Product of Example I per ton of the Basal Ration described in Example VII above. The same number and size chick treatment groups were used in this test as in Example VIII above.

A summary of the four week results is presented in Table III. It will be noted that a level of 6.25 g/T resulted in little or no activity, and that noticeable growth promotion began at 12.5 g/T. Subsequent improvements in weight gain and feed efficiency were noted at 25 and 50 g/T, with substantial improvements still being observed at 200 g/T. An unexplained absence of weight gain improvement (but not feed efficiency) was noted at 100 g/T. This type of occasional inconsistency is quite common in biological testing work. A sharp downturn was noted at a level of 400 g/T. On this basis of this "titration" test, from the standpoint of economics and efficacy, it would appear that a level of 25 g/T would be the optimum concentration.

TABLE III

| Group | No. Chicks | Treatment | Average 4 Week Performance Gain (g) | Average 4 Week Performance Feed Efficiency | Improved Response Over Basal Ration (%) Gain | Improved Response Over Basal Ration (%) Feed Efficiency |
|---|---|---|---|---|---|---|
| 1 | 32 | Basal Ration | 739.9 | 1.715 | — | — |
| 2 | 32 | Basal Ration + Product of Example I (6.25 g/T) | 714.6 | 1.657 | −3.4 | +3.4 |
| 3 | 32 | Basal Ration + Product of Example I (12.5 g/T) | 765.3 | 1.652 | +3.4 | +3.7 |
| 4 | 32 | Basal Ration + Product of Example I (25 g/T) | 805.7 | 1.603 | +8.9 | +6.5 |
| 5 | 32 | Basal Ration + Product of Example I (50 g/T) | 785.3 | 1.609 | +6.1 | +6.2 |
| 6 | 32 | Basal Ration + Product of Example I (100 g/T) | 742.7 | 1.663 | +0.4 | +3.0 |
| 7 | 32 | Basal Ration + Product of Example I (200 g/T) | 782.5 | 1.609 | +5.8 | +6.2 |
| 8 | 16 | Basal Ration + Product of Example I (400 g/T) | 751.5 | 1.678 | +1.6 | +2.2 |

EXAMPLE X

This example compares growth promotion activity of the product of Example I with other growth promotants at a concentration of 25 g/T in the Basal Ration described in Example VII. The other growth promotants include the product described in Example I of U.S. Pat. No. 3,542,784 — Burch and quinoxaline-1,4-dioxide. Day old broiler cross chicks were weight equalized into groups of eight chicks each, and four replicates of eight chicks each were fed the experimental rations over a 4 week period.

A summary of the four week body weight gains and feed efficiencies is presented in Table IV. It will be noted that the product of Example I gave the strongest response in growth rate and feed efficiency. The product of Example III of U.S. Pat. No. 3,542,784 — Burch appeared to give a growth response in this test but with a slight, if any, effect on feed efficiency while quinoxaline-1,4-dioxide did not have any apparent effect in this test.

TABLE IV

| No. Chicks | Treatment | Average 4 Week Performance Gain (g) | Average 4 Week Performance Feed Efficiency | Improved Response Over Basal Ration (%) Gain | Improved Response Over Basal Ration (%) Feed Efficiency |
|---|---|---|---|---|---|
| 32 | Basal Ration | 765.0 | 1.552 | — | — |
| 32 | Basal Ration + Product of Example I of U.S. 3,542,784 — Burch (25g/T) | 809.5 | 1.525 | +5.8 | +1.7 |
| 32 | Basal Ration + Product of Example III (25g/T) | 812.7 | 1.503 | +6.2 | +3.2 |
| 32 | Basal Ration + Quinoxaline-1,4-dioxide (25g/T) | 756.6 | 1.550 | −1.1 | +0.1 |

EXAMPLE XI

The growth promotion tests described in Example X were repeated with the exception that five replicates of eight chicks each were fed the formulations described in Table V for 4 weeks. A summary of the 4 week body weight gains and feed efficiencies is also presented in Table V. It will be noted that the product of Example I showed a moderate improvement in growth rate and a substantial improvement in feed efficiency, while the two antibiotics used commercially as growth stimulants, bacitracin and chlortetracycline, showed slight improvements in growth rates and moderate improvements in feed efficiencies. Addition of quinoxaline-1,4-dioxide to the Basal Ration resulted in an improvement in feed efficiency, but with a questionable effect on growth. Addition of 25 g/T of the product of Example I and 25 g/T of bacitracin to the Basal Ration produced synergistic effects. This growth response obtained from the product of Example I above that provided by bacitracin confirms the findings observed in Example XI.

EXAMPLE XII

The growth promotion tests described in Example X were repeated with the additional testing the products of Examples II and III. A summary of the 4 week body weight gains and feed efficiencies is presented in Table VI. These tests were then repeated with five replicates of eight chicks each to obtain the results presented in Table VII. Results in Tables VI and VII show the product of Example III of U.S. Pat. No. 3,542,784 — Burch had essentially no effect on growth rate or feed efficiency in either test. The product of Example I gave moderate improvements in production parameters in both tests. Table VI shows the products of Examples II and III gave moderate improvements in the first set of tests, while Table VII shows the product of Example III gave a more substantial response in the second set of tests.

TABLE VI

| No. Chicks | Treatment | Average 4 Week Performance Gain (g) | Feed Efficiency | Improved Response Over Basal Ration (%) Gain | Feed Efficiency |
|---|---|---|---|---|---|
| 32 | Basal Ration | 744.0 | 1.634 | — | — |
| 32 | Basal Ration + Product of Example II (25g/T) | 773.0 | 1.580 | +3.9 | +3.3 |
| 32 | Basal Ration + Product of Example III (25g/T) | 766.9 | 1.597 | +3.1 | +2.3 |
| 32 | Basal Ration + Product of Example I (25g/T) | 762.1 | 1.623 | +2.4 | +0.7 |
| 32 | Basal Ration + Product of Example III of U.S. 3,542,784 — Burch (25g/T) | 736.9 | 1.675 | −1.0 | −2.5 |

TABLE VII

| No. Chicks | Treatment | Average 4 Week Performance Gain (g) | Feed Efficiency | Improved Response Over Basal Ration (%) Gain | Feed Efficiency |
|---|---|---|---|---|---|
| 40 | Basal Ration | 682.5 | 1.785 | — | — |
| 40 | Basal Ration + Product of Example I (25g/T) | 695.3 | 1.706 | +1.9 | +4.4 |
| 40 | Basal Ration + Product of Example I of U.S. 3,542,784 — Burch (25g/T) | 668.1 | 1.737 | −2.1 | +2.7 |
| 40 | Basal Ration of Product of Example II (25g/T) | 696.4 | 1.672 | +2.0 | +6.3 |
| 40 | Basal Ration of Product of Example III (25g/T) | 723.7 | 1.669 | +6.0 | +6.5 |

EXAMPLE XIII

This example demonstrates the effects of the product of Example I in swine rations on growth rate and feed efficiency. Thirty-six weanling pigs weighing approximately 30 pounds each in good physical condition and originating from a common source were used in these tests. The pigs were allocated into sex and weight equalized pens of six pigs each. A 1 week period was allowed for acclimatization before testing. Three replicates of six pigs were fed the basal ration described below, and three replicates were fed the same basal

TABLE V

| No. Chicks | Treatment | Average 4 Week Performance Gain (g) | Feed Efficiency | Improved Response Over Basal Ration (%) Gain | Feed Efficiency |
|---|---|---|---|---|---|
| 40 | Basal Ration | 732.8 | 1.802 | — | — |
| 40 | Basal Ration + Quinoxaline-1,4-dioxide (25g/T) | 740.8 | 1.709 | +1.1 | +5.2 |
| 40 | Basal Ration + Bacitracin (25g/T) | 741.3 | 1.746 | +1.2 | +3.1 |
| 40 | Basal Ration + Chlorotetracycline (25g/T) | 752.5 | 1.717 | +2.7 | +4.7 |
| 40 | Basal Ration + Product of Example I (25g/T) | 756.1 | 1.677 | +3.2 | +6.9 |
| 40 | Basal Ration + Product of Example I (25g/T) + Bacitracin (25g/T) | 766.4 | 1.666 | +4.6 | +7.5 | ration supplemented with 25 g/T of the product of Example I.

The basal ration was a 17% commercial corn-soya pelletized formulation which was free of antibiotic and drug components. Composition of the basal ration formulation was:

| Ration Ingredient | 17% Pig Starter Formula |
|---|---|
| Ground Yellow Corn | 62.00 |
| Soybean Meal (50%) | 16.50 |
| Meat & Bone Scraps (50% Prot.) | 5.00 |
| Ground Oats | 15.00 |
| Ground Limestone | 0.25 |
| Dicalcium Phosphate | 0.50 |
| Salt | 0.50 |
| *Vitamin-Trace Mineral Premix | 0.25 |

*This premix provided the following supplemental vitamins and trace minerals per kilogram of finished Feed:

| | | |
|---|---|---|
| Vitamin A | = | 3300 I.U. |
| Vitamin D | = | 660 I.U. |
| Riboflavin | = | 3.3 mg. |
| Panto Acid | = | 13.2 mg. |
| Niacin | = | 17.6 mg. |
| Choline | = | 110 mg. |
| Vitamin $B_{12}$ | = | 17.6 mcg. |
| MSB Complex | = | 1.1 mg. |
| Copper | = | 9.9 mg. |
| Iron | = | 59.5 mg. |
| Iodine | = | 0.44 mg. |
| Manganese | = | 37.5 mg. |
| Zinc | = | 75 mg. |

The rations were offered ad libitum from six bushel self-feeders with a continuous supply of fresh water. The same ration formulations were used throughout the 6 week feeding period. Individual pig weighing were made after 0, 2, 4 and 6 (termination) week periods. Feed consumption records were kept on a pen basis, with feed efficiency conversion being compiled at the end of the second, fourth and sixth (termination) week of feeding. Complete morbidity and mortality records were kept.

Table VIII shows the results obtained with each of the six replicate pens of pigs when Group I (three replicates) were fed the basal ration and Group II (three replicates) were fed the basal ration supplemented with the product of Example I. The pigs fed with rations supplemented with the product of Example I showed a very substantial growth improvement and enhanced feed efficiency.

TABLE VIII

| Group | Treatment | No. Pigs | Replicate | Avg. Starting Wt. Per Pig | Avg. 6 Wk. Wt. Per Pig | Avg. Daily Gain | | Improved Response Feed/lb. Gain | | Over Basal Ration (%) Gain | Feed Efficiency |
|---|---|---|---|---|---|---|---|---|---|---|---|
| I | Basal Ration (Controls) | 6 | a | 32.0 | 92.5 | 1.440 | =1.399 | 2.639 | =2.568 | — | — |
| | | 6 | b | 32.0 | 92.2 | 1.433 | | 2.535 | | | |
| | | 6 | c | 31.8 | 87.5 | 1.325 | | 2.530 | | | |
| II | Basal Ration + Product of Example I (25 g/T) | 6 | a | 32.0 | 97.8 | 1.567 | =1.537 | 2.722 | =2.507 | +9.9 | +2.4 |
| | | 6 | b | 31.8 | 97.6 | 1.567 | | 2.392 | | | |
| | | 6 | c | 31.7 | 93.7 | 1.476 | | 2.406 | | | |

While the invention has been described with reference to certain specific embodiments thereof, it is understood that it is not to be so limited since alterations and changes may be made therein which are within the full and intended scope of the appended claims.

What is claimed is:

1. 2-[2-(5-nitro-2-furyl)vinyl]-4-(p-hydroxyanilino)-quinazoline.

2. The process of producing the compound of claim 1 comprising reacting 2-[2-(5-nitro-2-furyl)vinyl]-4-chloroquinazoline with p-aminophenol.

* * * * *

UNITED STATES PATENT AND TRADEMARK OFFICE
CERTIFICATE OF CORRECTION

PATENT NO. : 3,970,648

DATED : July 20, 1976

INVENTOR(S) : Herman Horn et al.

It is certified that error appears in the above—identified patent and that said Letters Patent is hereby corrected as shown below:

Columns 11 and 12, Table IV, under the heading "Treatment", "Example I" of second treatment should be --Example III--. Columns 11 and 12, Table IV, under the heading "Treatment", "Example III" of third treatment should be --Example I--. Columns 11 and 12, Table IV; Columns 13 and 14, Tables V, VI and VII, the heading "No. Chicks" should appear over the first column in each of the tables.

Signed and Sealed this

Twenty-first Day of July 1981

[SEAL]

Attest:

GERALD J. MOSSINGHOFF

Attesting Officer

Commissioner of Patents and Trademarks